United States Patent [19]

Houlihan et al.

[11] 4,107,311
[45] Aug. 15, 1978

[54] SPIRO[ISOINDOLINE-1,3'(4'H)-ISOQUINOLINE]-1',3-DIONES

[75] Inventors: William J. Houlihan, Mt. Lakes; Jeffrey Nadelson, Lake Parsippany, both of N.J.

[73] Assignee: Sandoz, Inc., E. Hanover, N.J.

[21] Appl. No.: 703,253

[22] Filed: Jul. 7, 1976

[51] Int. Cl.$^2$ .................. A61K 31/475; C07D 471/00
[52] U.S. Cl. .............................. 424/258; 260/287 K; 260/551 R
[58] Field of Search ..... 260/287 K, 287 CF, 287 CE; 424/258

[56] References Cited

PUBLICATIONS

Mondon et al., "Chemical Abstracts" (1970), vol. 73:4073(f).

*Primary Examiner*—Donald G. Daus
*Assistant Examiner*—David E. Wheeler
*Attorney, Agent, or Firm*—Gerald D. Sharkin; Robert S. Honor; Timothy G. Rothwell

[57] ABSTRACT

Substituted spiro[isoindoline-1,3'(4'H)-isoquinoline]-1',3-diones, e.g., 2,2'-dimethyl spiro[isoindoline-1,3'(4'H)-isoquinoline]-1',3-dione, are prepared by cyclizing α-(1-hydroxy-3-oxoisoindolin-1-yl)-o-toluamides and are useful as non-estrogenic anti-fertility agents.

5 Claims, No Drawings

SPIRO[ISOINDOLINE-1,3'(4'H)-ISOQUINOLINE]-1',3-DIONES

This invention relates to spiro isoindolines. More particularly, it relates to 2,2' dialkyl spiro(isoindoline-1,3' (4'H)-isoquinoline]-1', 3-diones, their preparation and their use in pharmaceutical compositions.

The compounds of this invention may be represented by the following structural formula:

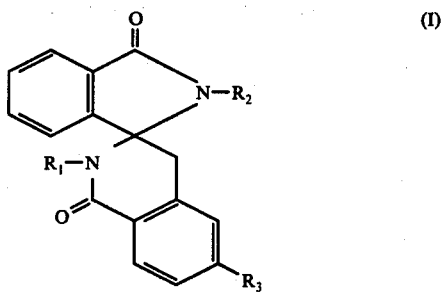

where
- $R_1$ and $R_2$ each independently represent straight chain lower alkyl, i.e., straight chain alkyl having 1 to 4 carbon atoms, e.g., methyl, ethyl, propyl, and the like and
- $R_3$ represents hydrogen, halo having an atomic weight of about 19 to 36, e.g., fluoro or chloro, lower alkyl, i.e., alkyl having 1 to 4 carbon atoms, e.g., methyl, ethyl, isopropyl, and the like, or lower alkoxy, i.e., alkoxy having 1 to 4 carbon atoms, e.g., methoxy, ethoxy, isopropoxy, and the like.

The compounds of formula (I) may be prepared by the following reaction scheme:

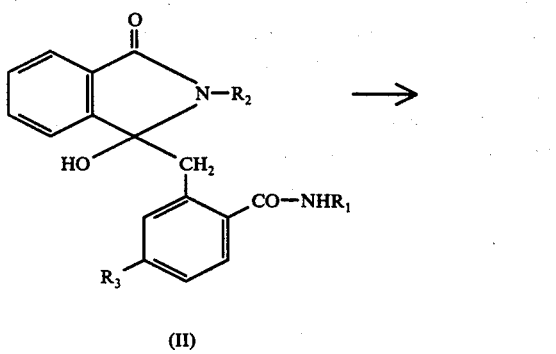

where $R_1$, $R_2$, and $R_3$ are as defined above.

The compounds of formula (I) are prepared by cyclizing a compound of formula (II) in the presence of a dehydration catalyst and optionally, in a solvent. The dehydration catalyst may be a dilute inorganic acid, such as sulfuric acid or hydrochloric acid when an aqueous solvent is used or thionyl chloride, phosphorus oxychloride, and the like when an organic solvent, such as an aromatic hydrocarbon, e.g., benzene, toluene, and the like is used. The particular solvent used is not critical. It is preferred that the reaction be carried out in dilute aqueous sulfuric acid. The temperature at which the reaction is carried out is not critical, but it is preferred that the reaction be run at about 50° C. to 150° C., preferably at the reflux temperature of the reaction medium. The time of the reaction also is not critical, but it is preferred that the reaction be run for 12 to 30 hours, especially 18 to 22 hours. The compounds of formula (I) are isolated by conventional techniques, e.g., evaporation and crystallization.

The compounds of formula (II) may be prepared in accordance with the following reaction scheme:

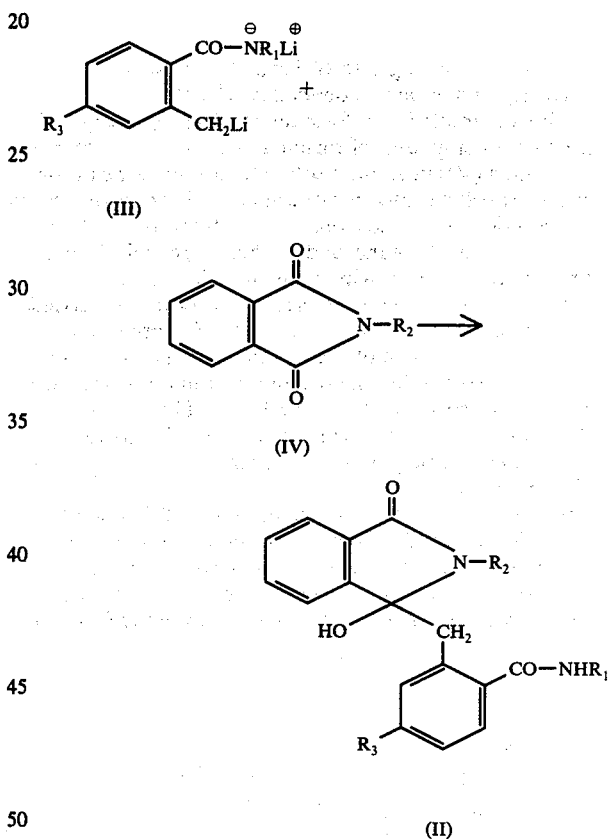

where $R_1$, $R_2$, and $R_3$ are as defined above.

The compounds of formula (II) are prepared by reacting a compound of formula (IV) with a compound of formula (III) in an inert solvent. Although the particular solvent used is not critical, it is preferred that the reaction be carried out in a solvent, such as hexane, diethyl ether, dioxane, tetrahydrofuran, and the like, especially tetrahydrofuran. The temperature at which the reaction is carried out is not critical, but it is preferred that the reaction be carried out between about 20° C. to 60° C., preferably between about 25° C. to 30° C. The time of the reaction also is not critical, but it is preferred that the reaction be run for 30 minutes to 4 hours, especially 1.5 to 2.5 hours. The compounds of formula (II) are isolated by conventional techniques, e.g., evaporation and crystallization.

The compounds of formula (III) may be prepared in accordance with the following reaction scheme:

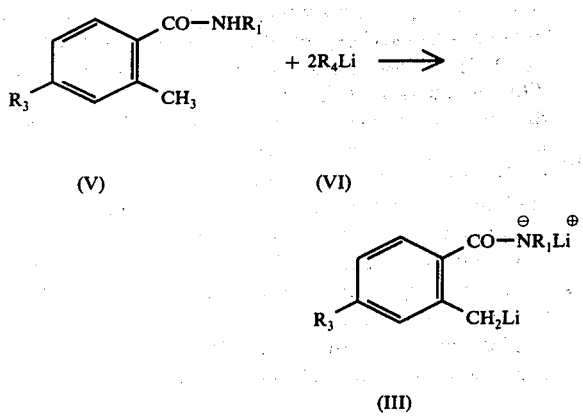

where
R₄ is alkyl having 1 to 6 carbon atoms and
R₁, R₂, and R₃ are as defined above.

The compounds of formula (III) are prepared by treating a compound of formula (V) with a compound of formula (VI) in an inert solvent. Although the particular inert solvent used is not critical, it is preferred that the reaction be carried out in a hydrocarbon solvent, such as hexane, heptane, and the like, especially hexane. The temperature at which the reaction is run is not critical, but it is preferred that the reaction be carried out between about −10° C. to +10° C., preferably at about 0° C. The time of the reaction also is not critical, but it is preferred that the reaction be run for 30 minutes to 4 hours, especially 1.5 to 2.5 hours. The compounds of formula (III) are normally used in the solvent in which they are prepared for preparing the compounds of formula (II).

It is to be noted that the compounds of formula (II) also exist in the following tautomeric form and said tautomeric forms are also included within this invention. For convenience, however, reference in the claims and text will be made only to compounds of the formula (II).

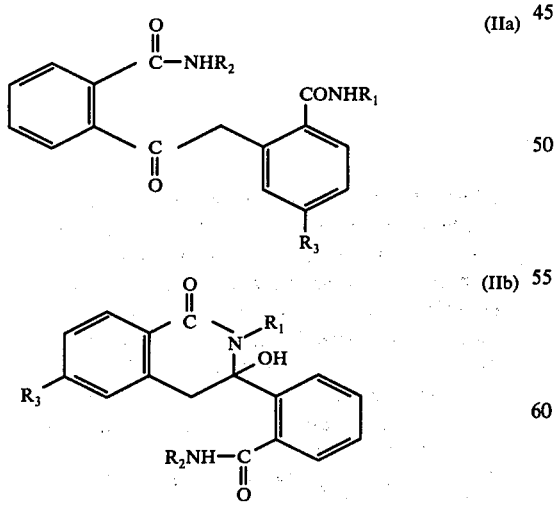

The compounds of formula (VI) and many of the compounds of formulas (IV) and (V) are known and are prepared by procedures disclosed in the literature. The compounds of formulas (IV) and (V) not specifically disclosed in the literature may be prepared by analogous methods using known starting materials.

The compounds of formula (I) are useful as antifertility agents as indicated by their having abortifacient activity.

Abortifacient activity is determined in female proestrous rats (Royal Hart, Wistar strain) selected from a colony and caged with fertile males. On the following day, pregnancy is confirmed by the presence of spermatozoa in the vaginal smear. On the seventh day following mating, the females are treated orally or subcutaneously with 1 to 30 milligrams of the compound to be tested. The animals are injected daily for a total of five days; and on the tenth to thirteenth day following the first injection, the animals are killed and the uterus checked for the presence or absence of implantation sites.

The compounds of formula (I), when used as antifertility agents exhibit none of the estrogenic effects and the side effects exhibited by the steroidal-type compounds used for these purposes.

When the compounds are employed for the above utility, they may be combined with one or more pharmaceutically acceptable carriers or adjuvants, and may be administered orally in such forms as tablets, capsules, elixirs, suspensions, and the like, e.g., bucally or subliqually as a tablet, parenterally in the form of an injectable solution or suspension or in special forms, such as suppositories, e.g., vaginal inserts, pessaries, and the like. Depending upon the compound and the mode of administration, the exact dosage utilized may vary.

In general, satisfactory results are obtained when the compounds of formula (I) are administered at a daily dosage of about 3.0 to about 250 milligrams orally, subcutaneously, or intramuscularly per kilogram of animal body weight. This daily dosage is preferably administered 1 to 4 times a day or in sustained release form. For most large mammals, such as primates, the total daily dosage is from about 180 milligrams primates, the total daily dosage is from about 180 milligrams to about 1500 milligrams. Dosage forms suitable for internal use comprise from about 45 milligrams to about 750 milligrams of the active compound in intimate admixture with a solid or liquid pharmaceutically acceptable carrier or diluent.

A representative formulation suitable for intramuscular administration once a day in fertility control is an injectable suspension prepared by standard techniques which contain the following:

| Ingredients | Weight (mg.) |
|---|---|
| 2,2′-dimethyl spiro[isoindoline-1,3′(4′H)-isoquinoline]-1′,3-dione | 200 |
| sodium carboxy methyl cellulose U.S.P. | 1.25 |
| methyl cellulose | 0.4 |
| polyvinylpyrrolidone | 5 |
| lecithin | 3 |
| benzyl alcohol | 0.01 |
| buffer agent to adjust pH for desired stability | q.s. |
| water | for injection q.s. to 2 milliliters |

EXAMPLE 1

2,2'-dimethyl spiro[isoindoline-1,3'(4'H)-isoquinoline]-1',3-diones

Step A:

α-(1-hydroxy-2-methyl-3-oxoisoindolin-1-yl)-N-methyl-o-toluamide

A solution of 29.8 grams (0.2 mole) of N-methyl-o-toluamide in 600 milliliters of dry tetrahydrofuran is treated dropwise with 275 milliliters (0.44 mole) of n-butyl lithium in hexane, while maintaining the temperature at 0° C. to 10° C. After the addition is complete, the mixture is stirred at 0° C. to 10° C. for 2 hours. The cooling bath is removed and a solution of 32.2 grams (0.2 mole) of N-methyl phthalimide in 330 milliliters of tetrahydrofuran is added dropwise. The temperature is maintained at 20° – 25° C. during the addition, afterwhich it is stirred for 1½ hours at room temperature. The resulting mixture is cooled in ice and quenched by the addition of saturated ammonium chloride. The layers are separated and the organic layer is washed with ammonium chloride solution, dried over magnesium sulfate, filtered and evaporated in vacuo. The resulting oil is crystallized from ethyl acetate to give α-(1-hydroxy-2-methyl-3-oxoisoindolin-1-yl)-N-methyl-o-toluamide, m.p. 175.5 – 177.5.

When the above reaction is carried out using an equivalent amount of N-methyl-4-fluoro-o-toluamide, N-methyl-4-methoxy-o-toluamide or N-methyl-4-methyl-o-toluamide in place of the N-methyl-o-toluamide, there is obtained: α-(1-hydroxy-2-methyl-3-oxoisoindolin-1-yl)-N-methyl-4-fluoro-o-toluamide, α-(1-hydroxy-2-methyl-3-oxoisoindolin-1-yl)-N-methyl-4-methoxy-o-toluamide, or α-(1-hydroxy-2-methyl-3-oxoisoindolin-1-yl)-N-methyl-4-methyl-o-toluamide, respectively.

Step B:

2,2'-dimethyl-spiro[isoindoline-1,3'(4'H)-isoquinoline]-1',3-dione

A mixture of 9.1 grams (0.0294 mole) of α-(1-hydroxy-2-methyl-3-oxoisoindolin-1-yl)-N-methyl-o-toluamide and 180 milliliters of 2 M sulfuric acid is refluxed for 20 hours. The mixture is cooled and the solid separated by filtration. The solid is then dissolved in methylene chloride and washed twice with water and once with brine. The organic phase is dried over magnesium sulfate, filtered and evaporated in vacuo. The resulting oil is crystallized from ethanol to give 2,2'-dimethyl spiro[isoindolin-1,3'(4'H)-isoquinoline]1',3-dione, m.p. 202° – 203° C.

Following the above procedure, but using an equivalent amount of α-(1-hydroxy-2-methyl-3-oxoisoindolin-1-yl)-N-methyl-4-fluoro-o-toluamide, α-(1-hydroxy-2-methyl-3-oxoisoindolin-1-yl)-N-methyl-4-methoxy-o-toluamide, or α-(1-hydroxy-2-methyl-3-oxoisoindolin-1-yl)-N-methyl-4-o-toluamide in place of the α-(1-hydroxy-2-methyl-3-oxoisoindolin-1-yl)-N-methyl-o-toluamide, there is obtained: 2,2'-dimethyl-6'-fluoro-spiro [isoindoline-1,3'(4'H)-isoquinoline]-1',3-dione, 2,2'-dimethyl-6'-methoxy-spiro[isoindoline-1,3'(4'H)-isoquinoline]-1',3-dione, or 2,2'-dimethyl-6'-methyl-spiro[isoindoline-1,3'(4'H)-isoquinoline]-1',3-dione, respectively.

The 2,2'-dimethyl-spiro[isoindoline-1,3'(4'H)-isoquinoline]-1',3-dione is an effective non-estrogenic antifertility agent when orally administered to an animal in need of said treatment at a dosage of 150 milligrams one to four times per day.

What is claimed is:

1. A compound of the formula

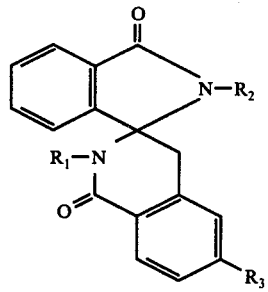

wherein $R_1$ and $R_2$ each independently represents straight chain lower alkyl having 1 to 4 carbon atoms and $R_3$ represents hydrogen, fluoro or chloro, lower alkyl having 1 to 4 carbon atoms or lower alkoxy having 1 to 4 carbon atoms.

2. The compound according to claim 1, which is 2,2'-dimethyl spiro[isoindoline-1,3'(4'H)-isoquinoline]-1',3-dione.

3. The compound according to claim 1 which is 2,2'-dimethyl-6'-methoxy-spiro[isoindoline-1,3'(4'H)-isoquinoline]-1',3-dione.

4. An abortifacient pharmaceutical composition comprising a compound according to claim 1 and a pharmaceutically acceptable carrier therefor.

5. A method of controlling fertility which comprises the step of internally administering to an impregnated mammal a therapeutically effective amount of a compound of claim 1.

* * * * *